United States Patent
Hiebert

(10) Patent No.: US 12,290,196 B2
(45) Date of Patent: May 6, 2025

(54) THERMAL RETENTION COVERINGS FOR USE WITH TEMPERATURE PROBES

(71) Applicant: Eugene Lloyd Hiebert, Salem, OR (US)

(72) Inventor: Eugene Lloyd Hiebert, Salem, OR (US)

(*) Notice: Subject to any disclaimer, the term of this patent is extended or adjusted under 35 U.S.C. 154(b) by 0 days.

(21) Appl. No.: 18/824,383

(22) Filed: Sep. 4, 2024

(65) Prior Publication Data

US 2024/0423392 A1   Dec. 26, 2024

Related U.S. Application Data

(63) Continuation-in-part of application No. 16/452,109, filed on Jun. 25, 2019.

(Continued)

(51) Int. Cl.
*G01K 13/20* (2021.01)
*A47G 9/02* (2006.01)
(Continued)

(52) U.S. Cl.
CPC ............ *A47G 9/0223* (2013.01); *G01K 1/14* (2013.01); *G01K 13/20* (2021.01); *A61B 5/00* (2013.01); *A61F 2007/0244* (2013.01)

(58) Field of Classification Search
CPC ........ A47G 9/0223; G01K 13/20; G01K 1/14; A61F 2007/0244; A61F 7/0097;
(Continued)

(56) References Cited

U.S. PATENT DOCUMENTS 4,313,993 A * 2/1982 McGlory ................. B32B 5/18
428/920
4,525,406 A 6/1985 Pollock
(Continued)

FOREIGN PATENT DOCUMENTS

AU    2003100663 B4 *  9/2003  ............... E04B 1/78
CN    101754898 A   *  6/2010  ......... A47J 41/0066
(Continued)

OTHER PUBLICATIONS

18824383_2024-11-13_AU_2003100663_B4_H.pdf,Sep. 11, 2003.*
(Continued)

*Primary Examiner* — Gail Kaplan Verbitsky
(74) *Attorney, Agent, or Firm* — Klarquist Sparkman, LLP

(57) ABSTRACT

Exemplary thermal retention coverings including a flexible fluid-impermeable outer shell having two outer layers sealed around their perimeters, one or more interior layers disposed between the outer layers, such as a flexible radiant barrier layer, an open cell layer or material, and/or a flexible thermal insulation layer, and a portal configured to receive a thermal probe into an interior space between a first one of the outer shell layers and the interior layers, the first outer shell layer including a patient side surface configured to oriented toward a patient. The covering is configured to retain patient body heat by creating a barrier to conductive, convective, and/or radiant patient body heat loss and is configured to enable improved monitoring of a temperature of a patient by monitoring the patient temperature from the interior space.

19 Claims, 8 Drawing Sheets

Related U.S. Application Data

(60) Provisional application No. 62/689,505, filed on Jun. 25, 2018.

(51) Int. Cl.
*A61B 5/00* (2006.01)
*G01K 1/14* (2021.01)
*A61F 7/02* (2006.01)

(58) Field of Classification Search
CPC ........ A61F 2007/0257; A61F 2007/025; A61F 2007/0249; A61F 2007/0253; A61F 2007/0255; A61F 2007/0266; A61F 2007/0288; B32B 5/245
See application file for complete search history.

(56) References Cited

U.S. PATENT DOCUMENTS

| | | | |
|---|---|---|---|
| 4,665,364 A * | 5/1987 | Hanawa | G01R 33/3621 324/309 |
| 4,884,303 A | 12/1989 | Scherer | |
| 4,889,135 A | 12/1989 | Poettgen | |
| 4,945,924 A | 8/1990 | Poettgen | |
| 4,961,238 A | 10/1990 | Limb et al. | |
| 5,146,634 A | 9/1992 | Hunt | |
| 5,191,895 A * | 3/1993 | Koltringer | A61B 5/4824 600/549 |
| 5,497,773 A * | 3/1996 | Kuhara | G01R 33/56554 324/318 |
| 6,138,676 A * | 10/2000 | Bruhn | A61B 46/00 128/853 |
| 6,511,501 B1 | 1/2003 | Augustine et al. | |
| 8,671,940 B2 * | 3/2014 | Allen | A61M 16/00 128/202.19 |
| 10,206,248 B2 * | 2/2019 | Augustine | A47C 21/048 |
| 2002/0019654 A1 | 2/2002 | Ellis et al. | |
| 2004/0088774 A1 | 5/2004 | Lawson | |
| 2007/0067910 A1* | 3/2007 | Augustine | A47G 9/0261 5/501 |
| 2008/0103567 A1* | 5/2008 | Augustine | A61F 7/0097 607/108 |
| 2009/0032516 A1* | 2/2009 | Reasor | H05B 3/36 383/61.3 |
| 2011/0137148 A1* | 6/2011 | Khizhnichenko | A61B 8/12 600/411 |
| 2012/0096641 A1 | 4/2012 | McGuire et al. | |
| 2014/0277307 A1 | 9/2014 | Gammons et al. | |
| 2016/0174868 A1* | 6/2016 | Tarasek | A61B 5/0051 600/411 |
| 2016/0278976 A1 | 9/2016 | Krüger | |
| 2017/0196381 A1 | 7/2017 | Lucas et al. | |
| 2018/0161196 A1* | 6/2018 | Lyytikainen et al. | A61F 6/18 |
| 2019/0059619 A1 | 2/2019 | Hood et al. | |

FOREIGN PATENT DOCUMENTS

| | | | | |
|---|---|---|---|---|
| CN | 202759962 U | * | 3/2013 | |
| CN | 204106306 U | * | 1/2015 | |
| DE | 10207793 A1 | * | 9/2002 | ........... A47G 9/0215 |
| DE | 202012009722 U1 | * | 8/2013 | ............. A47J 27/08 |
| DE | 2916110 C2 | * | 4/2020 | |
| EP | 0336443 A1 | * | 10/1989 | |
| JP | S60191324 U | * | 12/1985 | |
| JP | S62242528 A | * | 10/1987 | |
| JP | S635866 Y2 | * | 2/1988 | |
| JP | 3609123 B2 | * | 1/2005 | ......... A41D 13/0531 |
| JP | 3158476 U | * | 4/2010 | |

OTHER PUBLICATIONS

18824383_2024-11-13_CN_101754898_A_H.pdf,Jun. 23, 2010.*
18824383_2024-11-13_DE_10207793_A1_H.pdf,Sep. 5, 2002.*
18824383_2024-11-13_JP_3158476_U_H.pdf,Apr. 2, 2010.*
18824383_2024-11-13_JP_3609123_B2_H.pdf,Jan. 12, 2005.*
18824383_2024-11-15_CN_202759962_U_H.pdf,Mar. 6, 2013.*
18824383_2024-11-15_DE_202012009722_U1_H.pdf,Aug. 14, 2013.*
18824383_2024-11-15_EP_0336443_A1_H.pdf,Oct. 11, 1989.*
18824383_2024-11-13_JP_S60191324_U_H.pdf,Dec. 18, 1985.*
18824383_2024-11-13_JP_S62242528_A_H.pdf,Oct. 23, 1987.*
18824383_2024-11-13_JP_S635866_Y2_H.pdf,Feb. 18, 1988.*
Dodiuk et al., *Handbook of Thermoset Plastics*, "9.6.1 Polyurethane Foams," Elsevier, 3$^{rd}$ Edition, p. 285 (2014).
"Foam Factory, Seats & Cushions: Foam Types," Wayback Machine (May 8, 2017).
Horrocks et al., *Handbook of Technical Textiles*, "16.6 Thermal Insulation Materials," Woodhead Publishing, Figure 16.2, p. 433 (2000).
Manglik, *Heat Transfer and Fluid Flow Data Books*, "412.5 Emissivity," Genium Publishing Corporation, p. 24 (1990).
Szycher, *Szycher's Handbook of Polyurethanes*, "7.2 Types of Polyurethane Foam," Taylor & Francis, 2$^{nd}$ Edition, Table 7.1, p. 187 (2013).
Yam, Wiley Encyclopedia of Packing Technology—Foil, Aluminum, John Wiley & Sons, 3$^{rd}$ Edition, Table 1, p. 527 (2009).

* cited by examiner

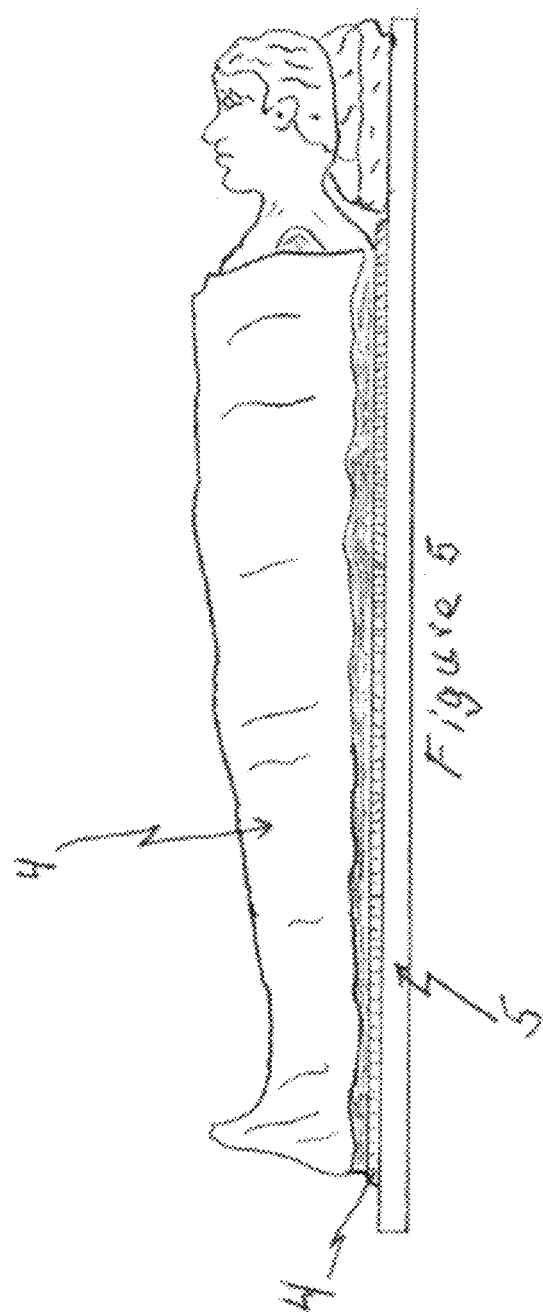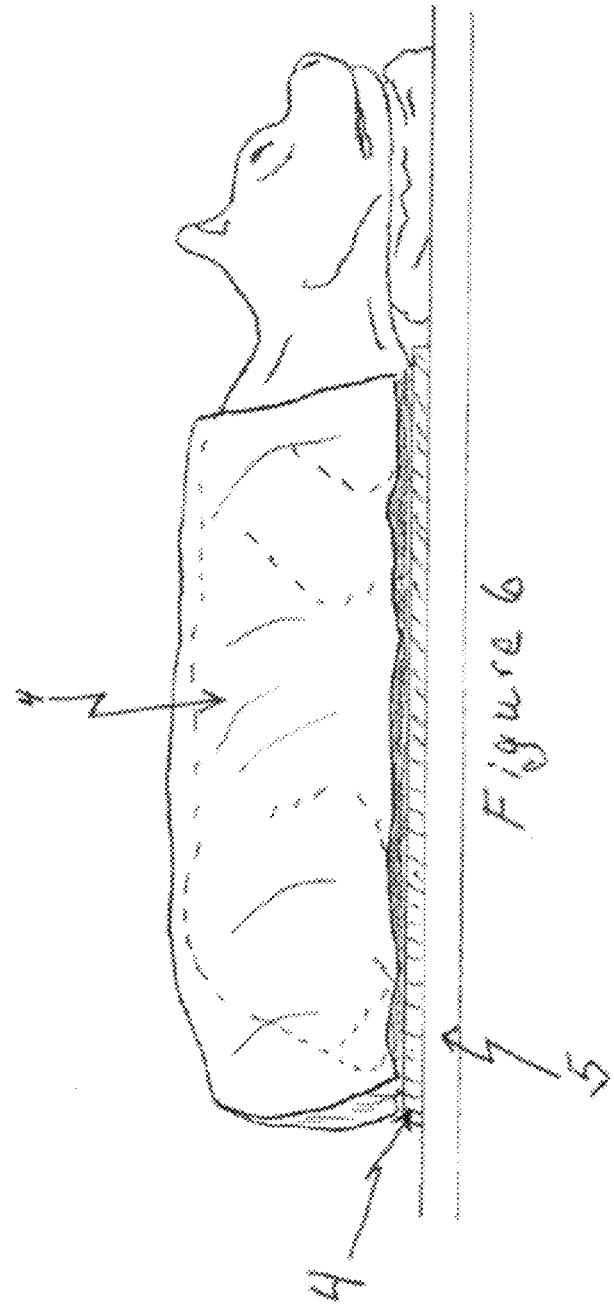
Figure 6

THERMAL RETENTION COVERINGS FOR USE WITH TEMPERATURE PROBES

CROSS-REFERENCE TO RELATED APPLICATIONS

This application is a continuation-in-part of U.S. patent application Ser. No. 16/452,109, which was filed on Jun. 25, 2019, and which claims the benefit of U.S. Provisional Patent Application No. 62/689,505, filed Jun. 25, 2018, each of which is incorporated by reference herein in its entirety.

FIELD

This application is related to devices and methods for reducing heat loss in patients, such as thermal retention coverings for use during medical procedures and rescue procedures, which can be adapted for use with a temperature probe.

SUMMARY

The thermal retention blankets disclosed herein can help maintain normothermic body temperature, especially in situations where active or mechanical warming may not be available. The disclosed thermal retention blankets can be soft and supple, and can be draped or placed over and/or under the patient's body as the situation warrants to retain the most body heat. The thermal retention blankets can prevent patient body heat loss by radiation, conduction, and convection. The thermal retention blankets can be formed in various sizes and shapes dependent on the coverage needed due to the size and anatomy of the patient.

Exemplary blankets can comprise a flexible fluid-impermeable outer shell having two outer layers sealed around their perimeters, a flexible radiant barrier layer positioned inside the outer shell and being reflective of radiant energy, and a flexible thermal insulation layer positioned inside the outer shell adjacent the radiant barrier layer and comprising a material having low thermal conductivity and providing insulation against conduction of heat through the blanket, such that the blanket is capable of retaining patient body heat by creating a barrier to conductive, convective, and radiant patient body heat loss.

In some embodiments, an air cell layer or material capable of entrapping air (e.g., open cell foam layer) can be included to provide a layer of air within the outer shell for additional thermal insulation. In some embodiments, the radiant barrier layer can be made of an MRI-compatible material, or can be removed (e.g., replaced by the air cell layer), to provide a blanket that is MRI-compatible and can retain a patient's body heat during MRI scanning.

The foregoing and other objects, features, and advantages of the disclosed technology will become more apparent from the following detailed description, which proceeds with reference to the accompanying figures.

BRIEF DESCRIPTION OF THE DRAWINGS

FIG. 5 shows a human laying supine on a support structure which has a thermal retention blanket between the superior surface of the support structure and the posterior aspect of the human. The human has a second thermal retention blanket draped over its anterior and lateral aspects. This is illustrative only.

FIG. 6 shows a dog laying with its ventral surface on a support structure. Between the superior surface of the support structure and the ventral surface of the dog there is one thermal retention blanket. Draped over the dorsal and lateral aspects of the dog is another thermal retention blanket. This is illustrative only.

DETAILED DESCRIPTION

Hypothermia is the most common thermal consequence of general anesthesia. Millions of humans and animals are anesthetized every year with anesthesia and surgical professionals struggling to maintain normothermia and the consequent deleterious physiological effects of hypothermia.

Hypothermia can be defined as the body temperatures below:
1) Human adults—below 35 degrees Centigrade
2) Human infants—below 36 degrees Centigrade
3) Dogs and cats—between 35.8 degrees Centigrade and 37 degrees Centigrade The majority of patient heat loss during anesthesia and surgery is through the skin by the processes of radiation, conduction and convection as defined below.
1) Radiation:
   Radiation is the major source of heat loss in surgical patients in which infrared radiant energy is transferred from the relatively warm patient to the environment.
2) Conduction:
   Conduction refers to the direct flow of heat from the body to the surrounding air, fluids or solid materials such as a metal surgical table.
3) Convection:
   Convection involves the physical movement of ambient air or fluids by which body heat is removed from the patient.

These three heat loss processes occur as core body heat redistributes to the periphery and the skin surface as a consequence of anesthetic induced peripheral vasodilation and depression of the hypothalamic thermoregulatory centers.

Hypothermia can occur in three phases following anesthetic induction:

Phase 1:

In the first hour of anesthesia there is a rapid decline in body temperature as a consequence of anesthetic induced peripheral vasodilation and lowering of the temperature threshold in the hypothalamus preventing the institution of normal physiologic thermoregulatory mechanisms. These processes allow a redistribution of body heat from the body core to the periphery where heat is lost primarily through the skin by radiation and convection.

Phase 2:

Over the next two hours of anesthesia, body temperature declines in a slower linear fashion as heat loss exceeds heat production. This occurs as a consequence of a decrease in metabolism and inhibition of heat production by thermoregulatory mechanisms in the hypothalamus by anesthetic drugs.

Phase 3:

Over the next three to four hours of anesthesia a core body temperature plateau is reached after which temperature stabilizes and remains relatively unchanged as a thermal steady state is achieved.

Figure 7:
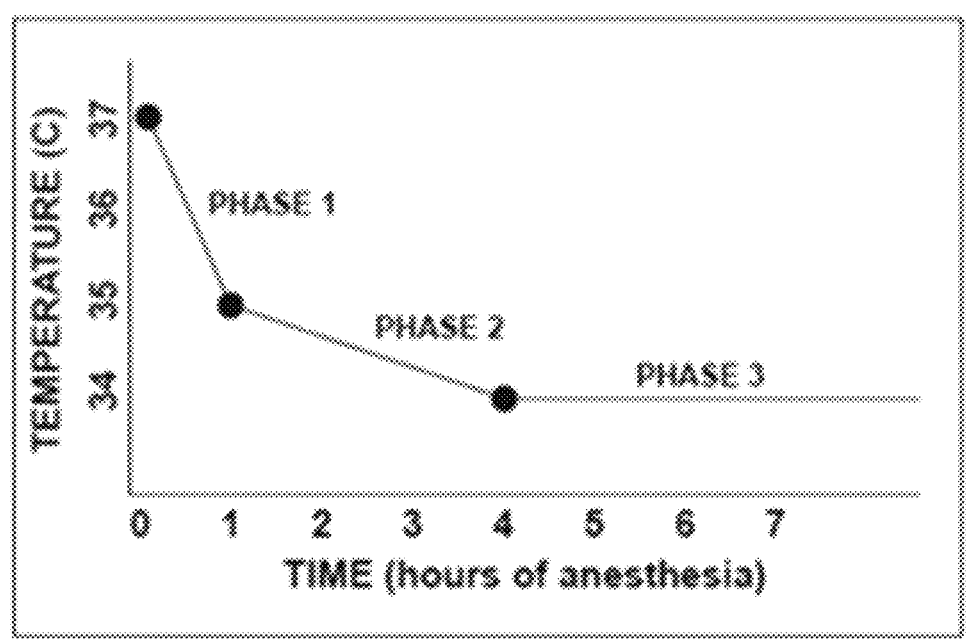
FIG. 7 is a graph that illustrates three phases of hypothermia.

The graph in FIG. 7 is illustrative of these three phases of hypothermia.

Prolonged hypothermia can lead to significant morbidity and mortality causing health care professionals to maintain body temperature during anesthesia as normothermic as possible. Deleterious consequences of hypothermia can be as follows:

Cardiac arrhythmias

Increased peripheral vascular resistance (vasoconstriction)

Decreased oxygen uptake by red blood cells

Coagulopathy and platelet dysfunction

Postoperative protein catabolism and stress response

Altered mental status

Impaired renal function

Decreased drug metabolism

Poor wound healing

Increased surgical site infections

Death

Current Warming Solutions:

Current solutions to hypothermia during anesthesia may be grouped into mechanical and nonmechanical methods. The mechanical methods include forced warm air from an electrical blower, electrical warming blankets and warm water circulating blankets which may be placed over and around the patient. Nonmechanical methods include regular blankets which have been warmed and "space blankets" which are essentially a sheet of aluminized foil to reflect body heat which are also placed over and around the patient. Most commercially available "space blankets" provide approximately 50 percent heat reflectivity and provide no barrier to conductive and convective body heat loss.

Thermal Retention Blankets:

The thermal retention blankets disclosed herein can help maintain normothermic body temperature, especially in situations where active or mechanical warming may not be available. The disclosed thermal retention blankets can be soft and supple, and can be draped or placed over and/or under the patient's body as the situation warrants to retain the most body heat. The thermal retention blankets can prevent patient body heat loss by radiation, conduction, and convection. The thermal retention blankets can be formed in various sizes and shapes dependent on the coverage needed due to the size and anatomy of the patient. Some of these situations where patient body heat retention is needed can include, but not limited to, when:

only a portion of the body is available for covering with the thermal retention blanket because the remainder of the body is part of a sterile field or being operated upon.

the patient is anesthetized for short procedures and active or mechanical warming is unnecessary or complicates the performance of the procedure.

the patient is receiving MRI imaging where no ferrous metal, such as that contained in mechanical warming devices, can be in the imaging room and the patient requires anesthesia so that accurate imaging studies can be obtained.

the patient is receiving CT imaging and there is not sufficient space for active or mechanical warming or it may complicate the procedure.

the patient is receiving X-ray imaging and laying on a cold table and in a cold room without active warming.

the patient has a large surface area to mass ratio and is, therefore, especially susceptible to rapid heat loss. Examples include human infants and small animals.

In some embodiments, the disclosed thermal retention blankets can comprise at four or more layers, including:

The outer two fluid impermeable layers or shells are sealed at their edges to hermetically enclose the inner layers. These outer layers can comprise any material that is impermeable or nearly impermeable to fluid such as, but not limited to, polyvinylchloride sheet, urethane sheet, etc. The edges of these layers or shells can be sealed in any manner that might be compatible with their physical and molecular structure such as, but not limited to gluing, heat sealing, radio frequency welding, etc.

One of the inner layers can comprise a flexible heat reflective layer or radiant barrier layer, which can be made of Mylar or aluminum, for example. In some embodiment, it can have equal or near equal heat reflectivity on each side. The radiant barrier layer can occupy most (e.g., more than 50%, more than 75%, more than 90%, more than 95%, up to 100%) of the interior surface area of the thermal retention blanket. The radiant barrier layer can have a high level (e.g., more than 50%, more than 75%, more than 90%, more than 95%, up to 100%) of reflectivity of radiant heat. An exemplary radiant barrier layer was shown by ASTM C1371 testing to have 5 percent emissivity and 95 percent reflectivity of radiant heat. The radiant barrier layer may have thickness from 2 to 8 mil (0.002 to 0.008 inches), for example.

One of the inner layers can comprise a flexible sheet of thermal insulation material having a low thermal conductivity. This thermal insulation sheet can have a sufficient thickness (e.g., at least ½ inch thick, or at least 1 inch thick) to provide a barrier to thermal conductivity. This thermal insulation sheet can be made of a material such as, but not limited to, polyethylene, polypropylene, rayon, or other insulation material which has low thermal conductivity. This thermal insulation sheet can comprise a fibrous material or a non-fibrous material. This thermal insulation sheet can occupy most (e.g., more than 50%, more than 75%, more than 90%, more than 95%, up to 100%) of the interior surface area of the thermal retention blanket, and may or may not be bonded to the heat reflective layer or radiant barrier layer.

The thermal retention blankets can retain patient body heat by creating a barrier to conductive, convective, and radiant patient body heat loss in the following manners:

Conductive Heat Loss:

The thermal retention blanket, by virtue of its thermal insulation layer, heat reflective layer or radiant barrier, and fluid impermeable outer shell, can form a thick insulating barrier to the direct conduction of heat from the body to the surrounding air or solid materials. In addition to being draped over the patient, it can also be placed underneath the patient to prevent conductive heat loss or direct transfer of heat to the underlying table or patient support surface.

Convective Heat Loss:

The thermal retention blanket drapes over the patient to form a physical barrier between the patient and the circulating ambient air. Thereby body heat is trapped under the thermal retention blanket and is not transported away by flowing convection currents in the ambient atmosphere.

Radiant Energy Loss:

The heat reflective layer or radiant barrier layer can be reflective of infra-red and other wavelengths of radiant energy on each side. In combination with the other layers, the heat reflective layer or radiant barrier layer is effective at substantially reducing radiant energy loss from the patient, reflecting most of the radiant energy from the patient back toward the patient. An exemplary radiant barrier layer has been shown by ASTM C1371 testing to reflect 95 percent of the radiant heat energy presented to it, mostly in the infra-red band.

Evaporative heat loss can also constitute a significant cause of heat loss in certain situations (e.g., with a wet or sweating patient). The disclosed thermal retention blanket can also prevent evaporative heat loss and loss of moisture from the body due to the fluid impermeable outer shell and the fluid impermeable radiant inner layer, which can also block water vapor and gasses from passing through the blanket as well.

The color of the external fluid impermeable shell can be significant as well in the retention of patient body heat. The colors close to the color black will tend to absorb relatively more heat and colors close to the color white will tend to reflect relatively more heat, which is the more preferable color range in the disclosed blankets. For example, dull black has an emissivity value of 0.94 and a reflectivity value of 0.06. This indicates that the dull black color absorbs 94 percent of the heat or energy presented to it and only reflects 6 percent of the heat or energy presented to it. Conversely, a shiny chrome color would reflect virtually all the heat or energy presented to it and absorb very little heat or energy. Therefore, colors toward the lighter end of the color spectrum are preferable such as white, yellow, orange, and red. These colors in addition to a shiny surface would further enhance their reflectivity of energy and patient body heat and would be preferable in the external shell.

Exemplary components of the thermal retention blankets, including the fluid impermeable outer shell, the inner radiant reflective layer, and the inner fibrous insulating layer, have undergone individual specifications testing. The results of these tests are provided in U.S. Provisional Patent Application No. 62/689,505, filed Jun. 25, 2018, which is incorporated by reference herein in its entirety. An exemplary thermal retention blanket, as a whole, has undergone rigorous ASTM testing as well.

An entire exemplary thermal retention blanket was subjected to ASTM C1371 testing which measures the heat emissivity and heat reflectivity of the blanket. The emissivity of the surface of a material is its effectiveness in emitting energy as thermal radiation or its ability for energy or heat to leave an object. The reflectivity of a surface is its effectiveness in reflecting energy or heat as thermal radiation away from its surface. Reflectivity and emissivity are inversely related. The greater the reflectivity of a substance, the less the emissivity. The emissivity of the thermal retention blanket was 30 percent and the reflectivity was 70 percent. The heat reflectivity of the blanket, as a whole, was less than the heat reflectivity of the inner radiant reflective layer by itself (95 percent) because of the intervening fluid impermeable outer shell and the inner insulating layer. This test (ASTM C1371) measures only radiant energy reflectivity and does not measure the thermal resistance or transmittance of the combined action of conduction, convection and radiation.

An entire exemplary thermal retention blanket with four layers (two outer fluid impermeable layers, a heat reflective layer or radiant barrier, and a fibrous insulation layer) was tested in accordance with ASTM standard test ASTM D1518. This test determines the thermal resistance or transmittance of the combined layers or materials between a hot plate and the ambient atmosphere. This test provides an indication of the resistance to heat loss by conduction, convection and radiation. The result of this test is expressed as a CLO value. The higher the CLO value the greater the resistance to heat flow from the hot plate to the ambient atmosphere. Testing was performed on three specimens with the radiant heat reflective layer or radiant barrier face up from the hot plate and the fibrous insulation face up from the hot plate with the results below

| Radiant barrier face up | CLO Value |
|---|---|
| Specimen 1 | 3.64 |
| Specimen 2 | 2.68 |
| Specimen 3 | 3.46 |
| Average | 3.26 |
| Fibrous insulation face up | |
| Specimen 1 | 3.67 |
| Specimen 2 | 2.85 |
| Specimen 3 | 3.52 |
| Average | 3.35 |

The CLO value of an article of clothing or blanket is not familiar to the consuming public. The information below compares familiar clothing ensembles to their corresponding CLO values to provide a frame of reference.

| Clothing Ensemble | CLO Value |
|---|---|
| Nude | 0 |
| Shorts only | 0.1 |
| Light summer clothing | 0.5 |
| Typical indoor clothing | 1.0 |
| Heavy business suit | 1.5 |
| Business suit, overcoat and hat | 2.0 |
| Extreme cold weather polar suit | 3 to 4 |

The average CLO values of 3.26 for radiant barrier up and the CLO value of 3.35 for the fibrous insulation up indicate the effectiveness of the thermal retention blanket in providing a barrier to conductive, convective and radiant body heat loss. As can be seen the CLO value of Specimen 2 is somewhat of an outlier compared to Specimens 1 and 3 and therefore if one takes the average of the CLO values of Specimens 1 and 3 the average CLO value would be 3.6. The consistency of CLO values for Specimens 1 and 3 with either side up indicates that there is equal effectiveness to heat resistance with either side up. The CLO value of the herein disclosed thermal retention blankets can be at least 3.0 or even at least 3.5, as seen on the above chart, which can be equivalent to or superior to that of an extreme cold weather polar suit.

The thermal retention blanket, because of its barrier to radiant, conductive and convective heat losses, is most effective during Phase 1 of hypothermia (FIG. 7), such as after anesthetic induction when there is a rapid drop in body temperature due redistribution of warm core body blood to the periphery as a consequence of peripheral vasodilation by anesthetic medications. Body heat is consequently lost through the peripheral skin mainly through radiation and convection and to a lesser extent through conduction and evaporation. The thermal retention blanket acts as a barrier to heat loss through these heat loss processes. It is, therefore, imperative to prevent as much body heat loss as possible, such as by placing the thermal retention blanket on the patient prior to anesthetic induction or as soon as possible after anesthetic induction to prevent this initial rapid decrease in body heat during Phase 1.

The Thermal Retention Blanket with its internal radiant and insulative layers has been proven in clinical trials, when used immediately upon induction of anesthesia, to be effective in maintain patient normothermia even during long surgical procedures. One case report indicated normothermia even after a four hour surgical procedure. Clinical trials also showed that no signal loss or artifact was observed when used in X-ray and CT imaging. The Thermal Retention Blanket has been proven to be effective in maintaining normothermia in surgical and dental procedures as well as X-ray and CT imaging without image signal loss.

The thermal retention blanket with its internal reflective layer and internal insulative layer as has been described above may be used for maintaining body temperature in situations such as, but not limited to, surgery and imaging procedures including X-ray and CT (Computerized Axial Tomography) scanning. When used, however, with MRI (Magnetic Resonance Imaging) scanning the Radio Frequency signal from the MRI scanner may react with the internal heat reflective layer (when it contains certain MRI-incompatible materials, such as metal material) to produce isolated areas of elevated temperature in the thermal retention blanket. This is not desirable and the thermal retention blanket with an MRI-incompatible internal reflective layer is, therefore, not recommended in MRI scanning.

Some embodiments of the herein disclosed thermal retention blankets can be compatible with MRI and used during MRI scanning. In some such embodiments, the internal reflective layer or radiant barrier can be replaced with an internal layer of material that entraps air such as open cell foam sheet. In some embodiments, the open cell foam sheet can be about ⅛ inch to about 1 inch in thickness, such as about ¼ inch to about ½ inch in thickness. The open cell foam sheet can cover most of the interior surface of the shell, like other internal layers. The open cell foam sheet can provide an insulating layer of air to prevent heat loss in addition to the internal fibrous insulative layer as described above. The density of the open cell foam can be from 0.9 to 3.0 pounds per cubic foot. The Indentation Load Deflection (IDL) of the open cell foam, which is a measure of compression resistance can be from 10 to 40. The higher the IDL number the firmer the foam. The IDL of foam can range from 8 to 120, with 8 being very soft and essentially no compression resistance with 120 being very hard. The IDL of 10 to 40 is preferable so that the foam is soft and supple allowing the blanket to drape loosely over and around the patient and also provide a layer of entrapped air. The side of the thermal retention blanket with the open cell foam sheet can be next to the patient to create a layer of insulating air with the fibrous insulative layer above it to prevent heat loss from this layer of air. Open cell foam as opposed the closed cell foam is preferred because open cell foam is more supple and pliable compared to closed cell foam, making it superior for use in a blanket application. Additionally, in open cell foam there is an interconnected network of bubbles or air cells which have open walls allowing entrainment of air throughout the open cell matrix. Air is an excellent insulator and, therefore, the insulating value of the open cell foam relates to the amount of air inside the matrix of interconnected air cells with open walls. In some embodiments, closed cell foam or analogous non-foam materials that provide an air or gas layer can be used alternatively to closed cell foam.

The open cell foam sheet may be made of materials such as, but not limited to, polyurethane, polyethylene, polyester and polyamide. Since these materials do not interact with the Radio Frequency signal from the MRI scanner, they will not create areas of elevated temperature in the blanket and may be utilized in the blanket for use in MRI scanning. The thermal retention blanket designed with the open cell foam layer instead of the heat reflective layer or radiant barrier is not limited to MRI scanning and may be used in other clinical applications as well. In other embodiments, the foam layer can be replaced with any other material that is capable of trapping air.

Other materials that are capable of entrapping air would include natural fibers such as spun cotton or synthetic microfibers such as but not limited to polyester, olefin and polypropylene to name a few. These materials can be made of single types of microfibers such as 100 percent polyester which may come in weights from 60 grams per meter squared to 200 grams per meter squared and from ¼ inch to 1 inch thick with a Thermal Resistance measured in CLO value from 0.9 to 3. Spun polyester microfibers can be manufactured with olefin and polypropylene fibers in a 55 percent polyester and 45 percent olefin mixture as well as a 55 percent polyester and 45 percent polypropylene mixture. These microfiber fabric mixtures may be in weights from 40 grams per meter squared to 220 grams per meter squared, thickness from 0.15 inch to 1 inch and a Thermal Resistance expressed as a CLO value of 0.8 to 3.5. These materials can also be, but not limited to, 100 percent olefin or 100 percent polypropylene. These are exemplary air trapping materials only and do not limit this invention to the materials or combinations of these materials. Other materials for example may include polyethylene with air bubbles manufactured into the material to create a layer of air as an insulator (similar to "bubble wrap").

The use of MRI scanning has become an essential imaging tool in human and veterinary medicine. Various metallic materials interfere with MRI imaging signals to effect imaging results and radio frequency signals from the MRI scanner can interact with various metallic materials to induce high temperatures in these materials. Consequently, no good methods of maintaining patient temperatures during long MRI scanning sessions have to this juncture been devised. Maintaining normothermia during MRI scanning sessions is essential to preventing morbidity and mortality during and after the MRI scanning session as has been previously described.

The disclosed thermal retention blankets designed for use with MRI have proven themselves to be effective maintaining normothermia and not interfering with MRI imaging signals in clinical trials. An exemplary thermal retention blanket was utilized as a clinical trial at an MRI center. It was found with multiple patients that normothermia was maintained even in scans over an hour in length and that there was no MRI signal loss despite using the thermal retention blanket in multiple different positions and there was also no inadvertent heating of the thermal retention blanket. This indicates that there is no undesirable interaction of the MRI signal with the components of the invention.

An exemplary thermal retention blanket compatible for MRI was also tested for inadvertent localized heating at an internationally recognized MRI compatibility testing laboratory with the following results. A single sample of a thermal retention blanket was tested for RF heating at both 1.5 T (64 MHz) and 3 T (128 MHz). A single sample was tested at both frequencies. A single heating test was conducted at each frequency (no repeats or variations were tested). All testing was generally conducted according to the relevant sections of ASTM F2182-11a:

RF exposure systems were used for 64 and 128 MHz exposure;

These systems were calibrated for RF power deposition ("Whole-body SAR") using calorimetric methods described in F2182;

The blanket was placed over the top of an ASTM phantom (as defined in ASTM F2182-11a) filled to a height of 9 cm with saline of conductivity verified to be between 0.45 and 0.5 S/m;

A finite number of fiber-optic temperature sensors were employed over the top surface of the blanket during exposure (7 in total); however, 7 fiber optic temperature probes were positioned at the corners, sides, and the middle of the blanket;

A thermal camera was used to obtain a measurement of the final temperature over the entire outer surface of the blanket following exposure at each frequency;

RF exposure was applied for a total of 20 minutes at each frequency.

The results of testing were as follows:

Following 20 minutes of exposure to a whole-body SAR level of 2.99+/−0.15 W/kg at 64 MHz:

peak temperature increases of not more than 0.2 deg-C were observed at the fiberoptic temperature sensors. Given that the detection limit of the sensors used was 0.1 deg-C, this result is consistent with the conclusion that no heating of the blanket could be detected at 64 MHz The thermal camera data indicate no localized heating or hot-spots.

Thermal photographs were taken of the device under test with 64 MHz, and the thermal camera images (before and immediately after RF exposure). No significant heating could be detected.

Following 20 minutes of exposure to a whole-body SAR level of 2.73+/−0.15 W/kg at 128 MHz:

peak temperature increases of not more than 0.6 deg-C were observed at the fiberoptic temperature sensors. Given that the detection limit of the sensors used was 0.1 deg-C, this result is consistent with the conclusion that very little heating of the blanket could be detected at 128 MHz The thermal camera data indicate no localized heating or hot-spots.

Thermographic photographs of the device under test with 128 MHz, and the thermal camera images (before and immediately after RF exposure). No significant heating could be detected.

These results indicate that the components of the thermal retention blanket configured for MRI do not interact with MRI signals to produce unwanted heating of the components of the Blanket.

As discussed above, the thermal blankets or covers disclosed herein can be effective in acting as a barrier to the four mechanisms of heat loss in the clinical settings. In such clinical settings, the patient often receives either general anesthesia, deep sedation or is medically compromised. In some examples, dependent on the type of clinical situation, it can be important that the patient's vital signs be monitored. In some examples, EKG, heart rate, blood pressure, end tidal CO2, oxygen saturation, and/or temperature can be monitored. In the above clinical situations, the patient may be predisposed to hypothermia for which the thermal covering is utilized to provide and/or maintain normothermia. It can therefore be useful that the patient's body temperature and the effectiveness of the patient warming technique be measured in order to monitor normothermia and determine whether additional warming techniques should be employed.

Heat loss during anesthesia, deep sedation and medically compromised situations is best understood by dividing the patient body into the core and peripheral compartments. The core compartment defined as the head, chest and abdomen, represents 50 to 60 percent of body mass. The temperature in the core compartment can remain relatively uniform. The peripheral compartment is comprised of the arms, legs, and skin, and, in the case of animals, the tail. The temperature in the peripheral compartment can be 3.6 degrees F. to 7.2 degrees F. cooler than the core compartment creating a temperature gradient between the core and peripheral compartments. The peripheral compartment temperature can fluctuate depending on the ambient temperature.

The core to peripheral compartment temperature gradient is normal. The gradient is controlled by the hypothalamus to mitigate heat loss to the environment. The hypothalamus redirects blood flow from the peripheral to the core compartment by peripheral vasoconstriction and increases metabolic heat production to maintain stable core compartment temperature. Neurogenic thermoregulation by the hypothalamus exists to maintain stable core compartment temperature.

General anesthesia causes a loss of neurogenic thermoregulation by the hypothalamus thereby redistributing warm core blood to the periphery. Virtually all anesthetic drugs are vasodilators which cause a loss of compensatory peripheral vasoconstriction. Consequently, warm core blood flows to the periphery where it is cooled by the four mechanisms of heat loss: conduction, convection, radiation, and evaporation. The patient can therefore undergo significant heat loss. Additionally, there can be a 20% to 40% decrease in metabolic rate and consequently a drastic drop in heat production. In contrast, when a patient is exposed to the elements and becomes hypothermic, there is peripheral vasoconstriction in the body's attempt to maintain normal core compartment temperature.

As discussed above, it can be useful to monitor a patient's temperature while under medical care. The peripheral or skin blood flow can be a determinant of the core compartment temperature and the temperature gradient (discussed above). The temperature of the skin or peripheral compartment can be correlated with the temperature of the core compartment as shown in the below examples.

Example: In humans, at an ambient temperature of 25 degrees C., the skin temperature of 34 degrees C. correlates with an internal or core temperature of 37 degrees C., a gradient of 3 degrees C.

Example: In animals, the normal temperature of a dog is 38.3 degrees C. to 39.2 degrees C. A dog rectal temperature of 38 degrees C. correlates with a snout temperature of 30.5 degrees C. and a paw temperature of 31.4 degrees C. indicating a temperature gradient of 6.6 degrees C. to 7.5 degrees C.

Body temperature measurements can be affected by parameters, such as, for example the selected parameters listed below and others.

Figure 1:
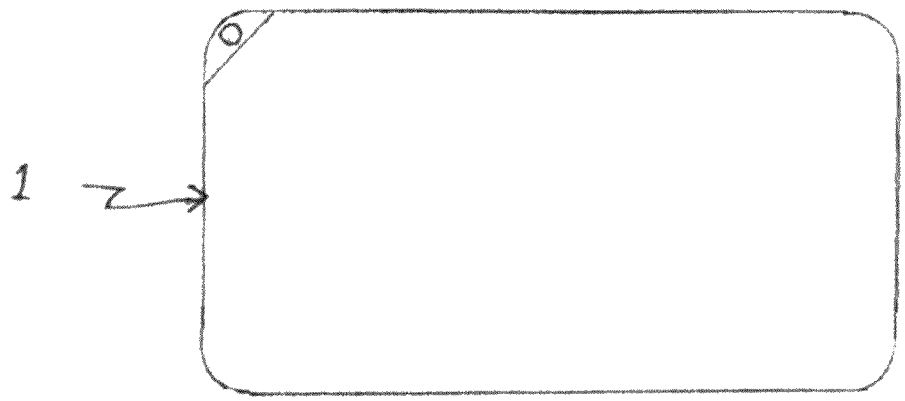
FIG. 1 is a plan view of an exemplary fluid impermeable external shell which comprises two outer layers, inside of which are a sheet of heat reflective layer or radiant barrier and a sheet of fibrous insulation material not shown in this figure. The two external fluid impermeable layers are sealed at their edges to form the shell. In the top left hand corner is a round grommet which is an example only and is not necessary for function. The grommet can be used to hang the blanket on a hook or attach it to something else.
Figure 2:
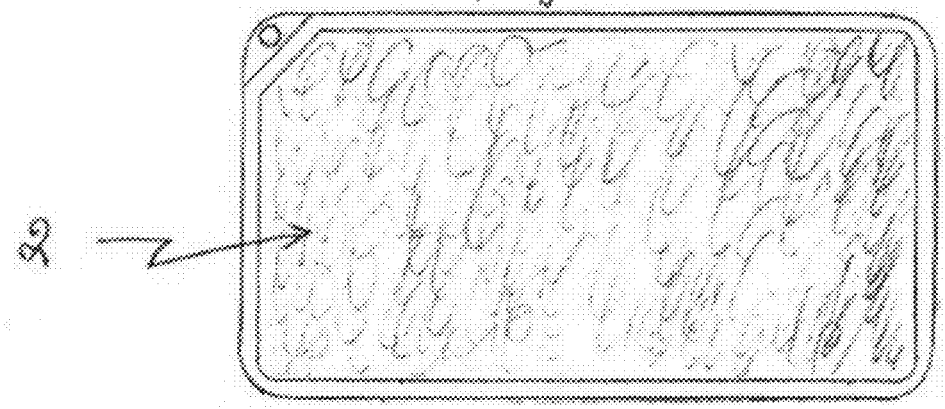
FIG. 2 shows a sheet of fibrous insulation that is positioned inside the fluid impermeable external shell. This is a sample shape only.
Figure 3:
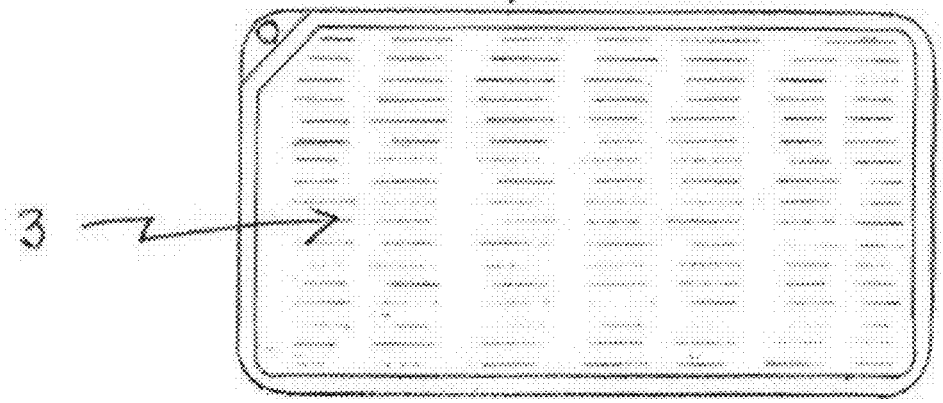
FIG. 3 shows a sheet of heat reflective or radiant barrier, which is positioned inside the fluid impermeable external shell. The sheet of heat reflective layer or radiant barrier may be substituted for or supplemented with a sheet of an exemplary open cell foam or other material capable of entrapping air. This is a sample shape only.
Figure 4:
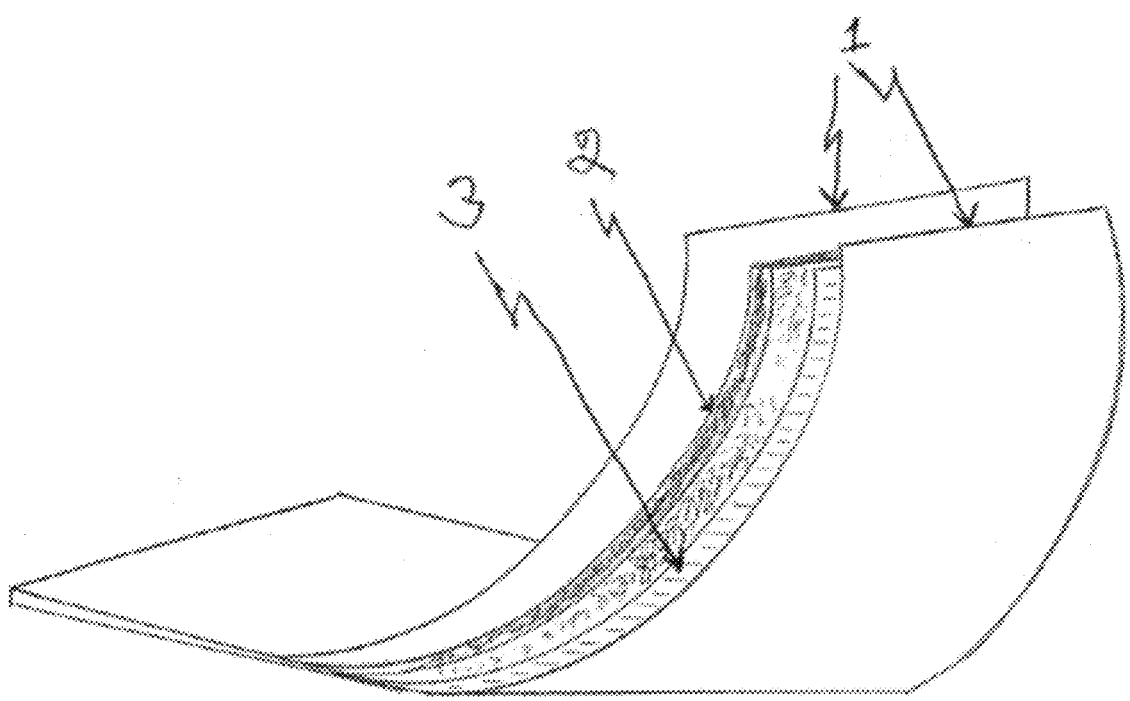
FIG. 4 shows four layers of an exemplary thermal retention blanket. Two external fluid impermeable layers, one inner layer of fibrous insulation and one layer of heat reflective or radiant barrier or open an exemplary open cell foam sheet. This is a sample construction only.
Figure 8:
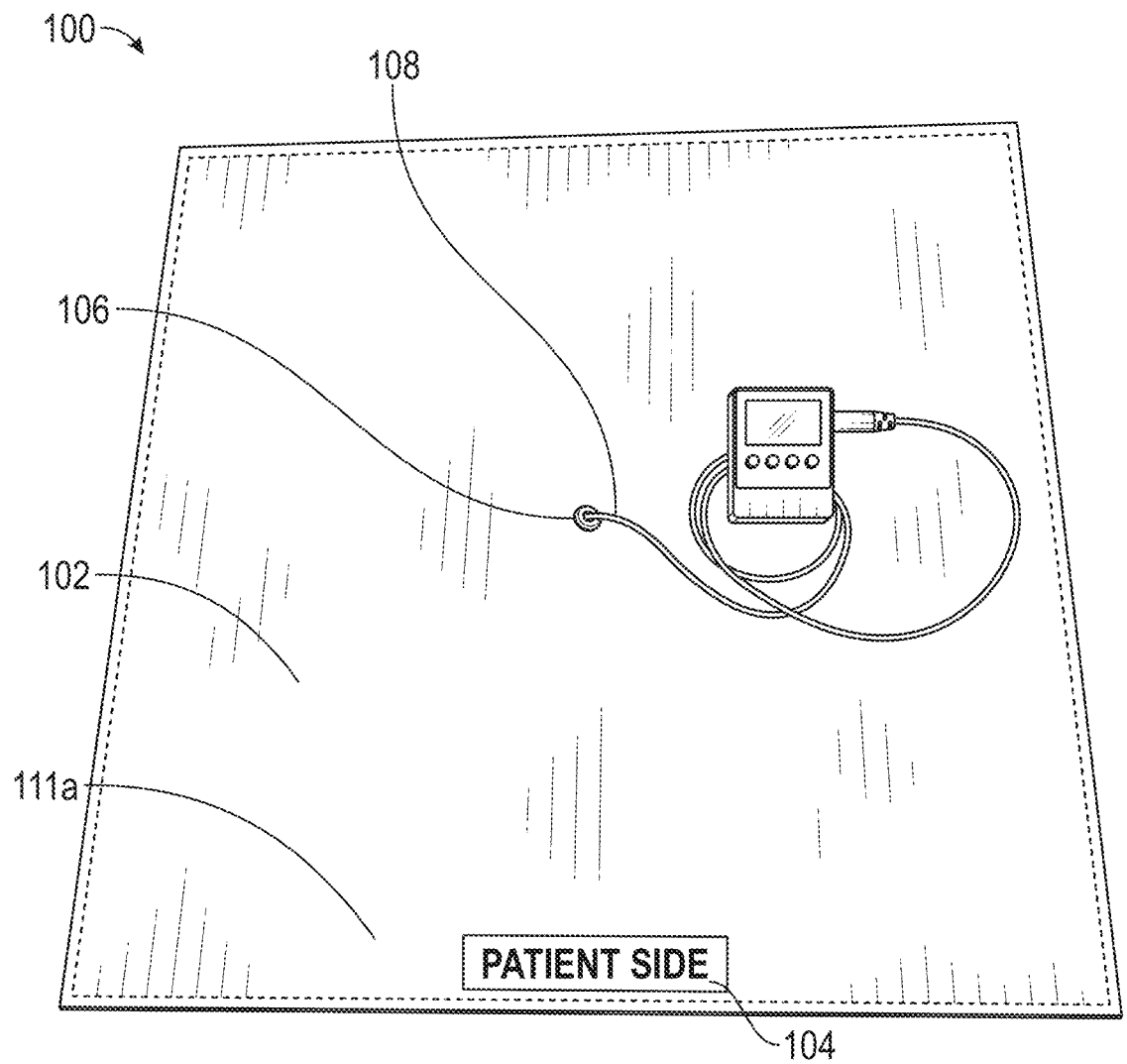
FIGS. 8-10 are top views of an exemplary thermal retention covering adapted for use with a temperature probe.
Figure 9:
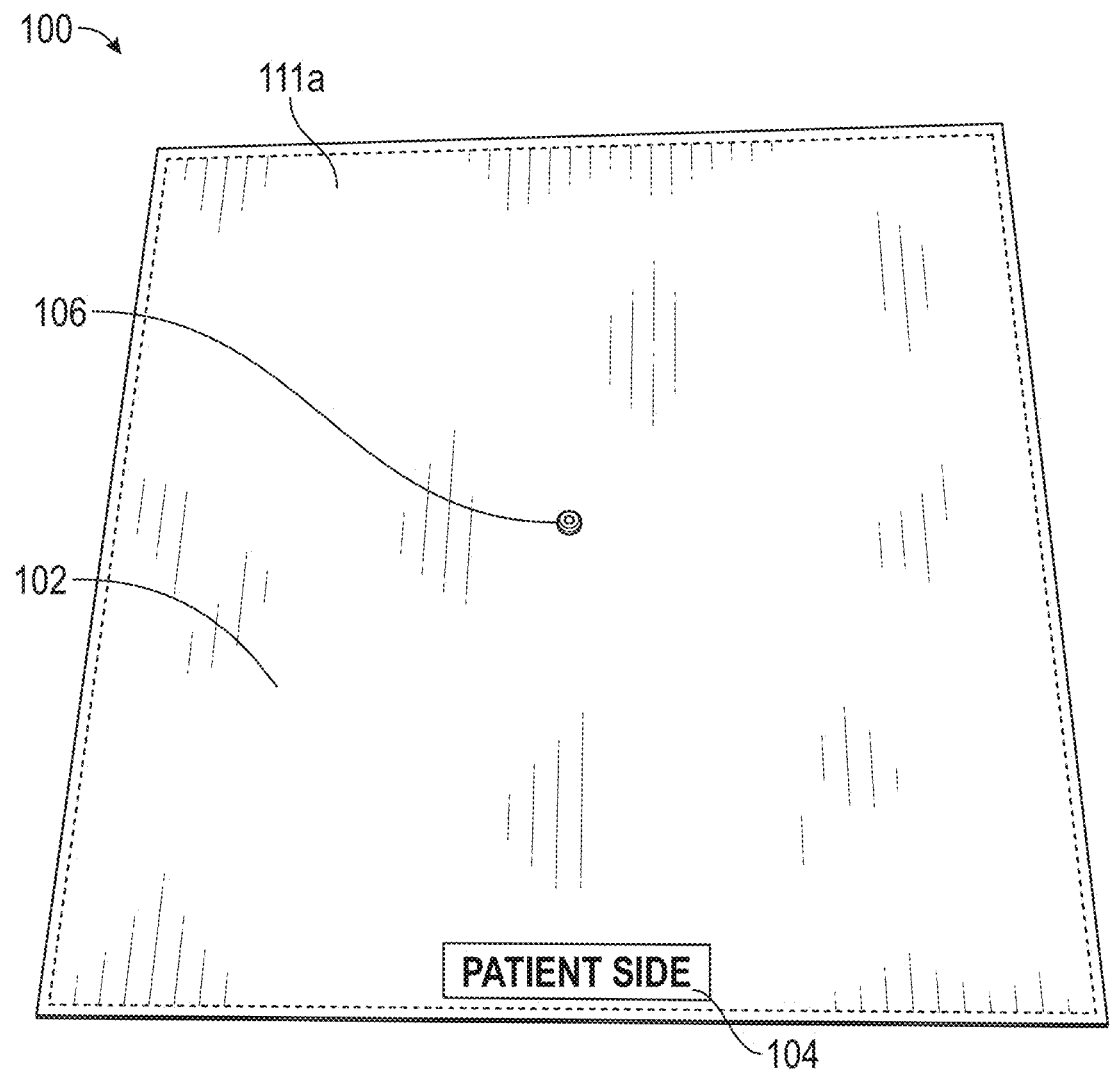
Figure 10:
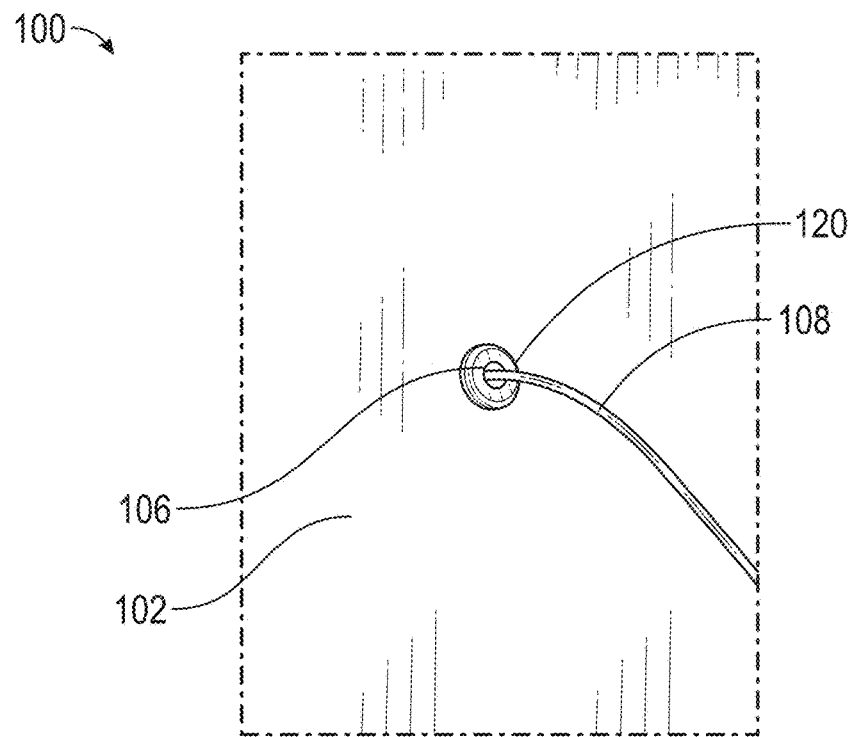
Figure 11:
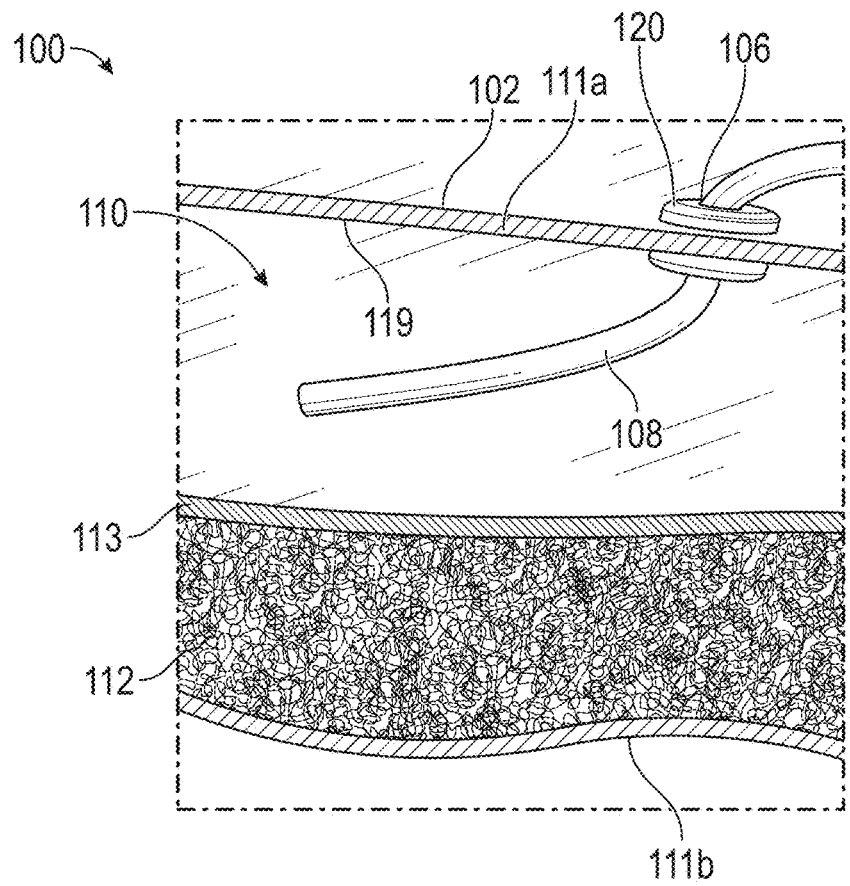
FIG. 11 is a cutaway view of the thermal retention covering shown in FIGS. 8-10.

1. Site of measurement—
   skin, oral cavity, ear, esophagus, rectum
2. Environmental conditions—
   ambient air temperature, ambient air flow, humidity, patient perspiration, patient body fluids, patient movement, movement of temperature probe
3. Temperature measurement technique—
   liquid crystal, thermocouple probe, infrared radiation reader, fiberoptic sensor In some examples, the core temperature of the patient is the best parameter of measurement and can be accomplished by measuring the esophageal or rectal temperature. However, when such areas for measurement are not available (for example, when these sites are not available, when inappropriate for the clinical situation, or where a patient has intolerance of an invasive temperature probe), a site on the skin surface can be utilized and a gradient correlation made with the core temperature. The use of the skin as a site of measurement, however, can create erroneous temperature readings as a consequence of, but not limited to, the situations below.

ambient air temperature
ambient air flow
ambient humidity
patient movement
movement or dislodgement of a temperature probe
patient perspiration
patient body fluids The thermal retention coverings adapted for use with and/or including one or more temperature probes described herein can overcome one or more of the foregoing causes of erroneous temperature readings on the skin and can therefore improve the accuracy of skin temperature readings. For example, a thermal retention covering 100 adapted for use with a temperature probe is shown in FIGS. 8-11. In some examples, the thermal retention covering 100 can have one more features of the thermal retention coverings and blankets discussed above and shown in FIGS. 1-6. For example, the thermal retention covering 100 can include two outer fluid impermeable layers or outer shell layers 111 (i.e., layers 111a, 111b) that are sealed at their edges (e.g., at a perimeter of the thermal retention covering 100) to hermetically enclose one or more inner layers. The inner layers can include a flexible heat reflective layer or radiant barrier layer 113 and/or a flexible sheet of thermal insulation material having a low thermal conductivity 112. In some examples, the layers 111, 112, and 113 are respectively similar to the layers 1, 2, and 3 shown in FIGS. 1-3 and described above. In an MRI-compatible version of the thermal retention cover 100, the radiant barrier layer 113 can be excluded or can be an MRI-compatible radiant layer and the inner layers can include a heat trapping or open cell foam layer adjacent to which is a heat insulative or fibrous insulating layer. In some examples, the thermal retention cover can include a heat trapping or open cell foam layer, a heat insulative or fibrous insulating layer, and a flexible heat reflective layer or radiant barrier layer. As shown in FIGS. 8 and 9, the thermal covering 100 can have a specified and/or identified patient side surface 102 for intimate and/or direct contact with a patient and/or the patient's clothing. In some examples, the patient side surface 102 can include an indicator 104 for identifying the patient side surface to a user. An exterior surface of the outer shell layer 111a can form the patient side surface 102 and the second shell layer 111b can form a second side surface (that is oriented away from the patient during use of the thermal retention covering) opposing the patient side surface 102.

The thermal retention covering 100 can be draped over or circumferentially wrapped around a patient, and after a period of time (e.g., several minutes) a steady temperature state can occur. The steady state can occur at the skin or patient surface, at the external surface of the covering, and/or at the interior space between the inside surface of the external material and the patient side of a heat reflective layer and/or a heat trapping layer of the covering—which can all have a same temperature. The space 110 between the inside surface of the external layer or shell 111a (which forms the patient side surface 102) and the adjacent layer(s) (e.g., layer 112 or 113) is an environmentally shielded location. Therefore, the temperature probe disposed in the interior space 110 may be protected from and/or may not be subject to the causes of the erroneous temperature readings, such as those as listed above. For example, the interior space 110 may be protected from and/or may not be subject to the ambient air temperature, ambient air flow, ambient humidity, patient perspiration, patient body fluids, patient movement or temperature probe movement or dislodgement. In some examples, the air within the interior space 110 can reach the steady state and temperature of the air within the interior space 110 can be measured and/or monitored. In some example, skin temperature of the patient can be monitored through the material of the fluid impermeable layer 111a while the temperature probe 108 is disposed within the interior space 110.

To measure temperature from the interior space 110, a hole or portal 106 can be included in the patient side surface 102 which extends through the fluid impermeable layer 111a. The diameter of portal 106 can be sized to have a thermocouple temperature probe 108 inserted through and/or seated within the portal. In some examples, a diameter of the portal 106 can be in a range of 10 mm to 30 mm. In some examples, a diameter of the portal 106 can be in a range of 1 mm to 10 mm greater than the diameter of the temperature probe 108. In some examples, the thermal retention covering can be one of a set of coverings each having different sized portals for use with different diameter temperature probes. The portal 106 can be in a location on the patient side surface 102 where the thermal covering will have optimal intimate contact with the patient surface. In some examples, the portal 106 can be disposed at a center or at an approximate center of the patient side surface 102. In some examples, multiple portals can be placed at several different locations on the patient side surface 102 so that monitoring site options can be customized according to the clinical need or situation and/or the patient anatomy. For example, the patient side surface 102 can include one or more rows of portals that are evenly dispersed relative to others of the portals. In some examples, multiple portals can be concentrically arranged around a central portal on the patient side surface 102.

In some examples, a distal end portion of the flexible temperature probe 108, whether it be a thermocouple or fiberoptic probe, can be passed into the portal 106 and advanced by a selected and/or predetermined distance (e.g., one to five inches) into the interior space 110 between the external patient side surface 102 and the adjacent interior layer 113. An opposing end of the probe 108 can be connected to a temperature monitor or to a transmitter for communication with a temperature monitor. In some examples, where the thermal covering includes multiple portals, additional temperature probes can be utilized with the thermal retention cover to monitor a temperature of the patient at multiple locations. In such examples, temperatures at the multiple locations can be averaged (e.g., an average of one or more core compartment temperatures and one or more peripheral compartment temperatures) to monitor an average patient temperature and/or temperatures of multiple locations can be individually monitored (e.g., a core compartment temperature and a peripheral compartment temperature).

In some examples, insertion of and/or seating of the temperature probe(s) 108 through the portal(s) 106 and into the interior space 110 can increase accuracy in temperature monitoring. For example, by providing for the temperature probe 108 to be inserted through the portal 106 and into the interior space 110, accuracy in temperature monitoring of the patient (e.g., skin or surface and core patient body temperature) is increased because the temperature probe is closer to a targeted portion of the patient (e.g., a portion of the core compartment, a portion of the peripheral compartment, an exposed portion of the patient uncovered from clothing and/or hair or fur, etc.) and is protected from exterior influences described above (e.g., ambient air, patient perspiration, body fluids, etc.). Further, accuracy can be increased by maintaining a position of the temperature probe so that, for example, temperature in a localized region can be monitored and changes detected and/or dislodgement of the probe can be prevented when moving or repositioning the patient during a procedure.

In some examples, insertion of the temperature probe 108 through the portal 106 and into the interior space 110 can protect the probe from damage, breaking, and/or wear during use. For example, having the probe inserted through the portal and housed within the interior space can provide increased protection from damage and wear to the probe (e.g., from handling, contact with the patient, patient fluids, and/or the support surface, and even in cases where the patient and thermal cover may be inadvertently bumped against or dropped from the support surface) relative to conventional temperature monitoring techniques. As noted above, having the probe 108 inserted through the portal 106 also makes it easier to reposition the patient without disruption of temperature monitoring and eases interference between the patient and the distal end portion of the probe, for example, during a procedure or during preparation for a procedure. The thermal retention covering 100 can additionally enable easy removal of the temperature probe from the patient post-procedure. For example, a practitioner can simply remove the thermal retention covering 100 from the patient and simultaneously remove the temperature probe 108.

In some examples, the temperature probe can be insertable into and removable from thermal retention covering 100. For example, the frictional forces between the exterior surface of the temperature probe 108 and the material of the shell layer 111 at and/or adjacent to the portal 106, for example, when the covering 100 is wrapped around a patient, can retain a position of the temperature probe 108 relative to the portal 106. As discussed above, the diameter of portal 106 can be designed to have the thermocouple temperature probe 108 inserted through the portal. In some examples, the diameter of the portal can be designed and/or selected to retain the position of the temperature probe relative the portal. For example, the diameter of the portal 106 can be about the same as a diameter of the temperature probe 108 (for example, 1% to 10% larger than the diameter of the temperature probe). In some examples, the diameter of the portal 106 can be in a range of 1 mm to 10 mm greater than the diameter of the temperature probe 108. In this way, lateral (side-to-side) movement of the temperature probe 108 within the portal 106 can be limited or prevented. Further, contact between the exterior surface of the probe 108 and the material of the shell layer 111 can be maximized on one or both of the patient side surface 102 and the opposing interior surface 119 of the shell layer 111a in order to resist inadvertent withdrawal of the probe 108 from the portal 106. In some examples, the diameter of the portal 106 can additionally be designed and/or selected to enable easy removal or uncoupling of the probe 108 from the thermal covering 100. For example, the frictional forces between the portal 106 and the probe 108 to enable a user to lightly pull on the probe (e.g., upward, downward, and/or away from the cover depending on a position of thermal retention covering) for its removal from the portal.

In some examples, the hole or portal 106 can include a grommet 120 which can be glued, welded or kept in place with friction between edges of the portal 106 and a circumferential groove in the grommet 120. In some examples, the grommet 120 reinforces the portal 106 to prevent tearing or stretching of the material surrounding the portal. In some examples, the grommet 120 forms or provides a raised annular structure on each of the interior side surface and the patient side surface 102 of the outer shell layer 111a. In some examples, the grommet can be formed from a metallic material, a plastic material, a rubber material, or another material or combinations thereof.

Frictional forces between the grommet 120 and an exterior surface of the temperature probe 108 can retain a position of the temperature probe relative to the grommet 120. In some examples, the grommet 120 increases a surface area of the portal 106 relative to the material of the outer shell layer 111a at the portal 106 without the grommet. In some example, the grommet can include a high friction coating. For example, when comprised of metal, the grommet 120 can include a coating comprising nickel diamond, tungsten carbide, ceramic, or other materials or combinations of materials. When comprised of plastic, the grommet 120 can include a coating comprising polyurethane, epoxy, silicone, fluorpolymers, or other materials or combinations of materials. In some examples, the grommet 120 can include a textured surface, such as a rough surface, to increase friction between the grommet and the exterior surface of the probe 108.

Figure 12:
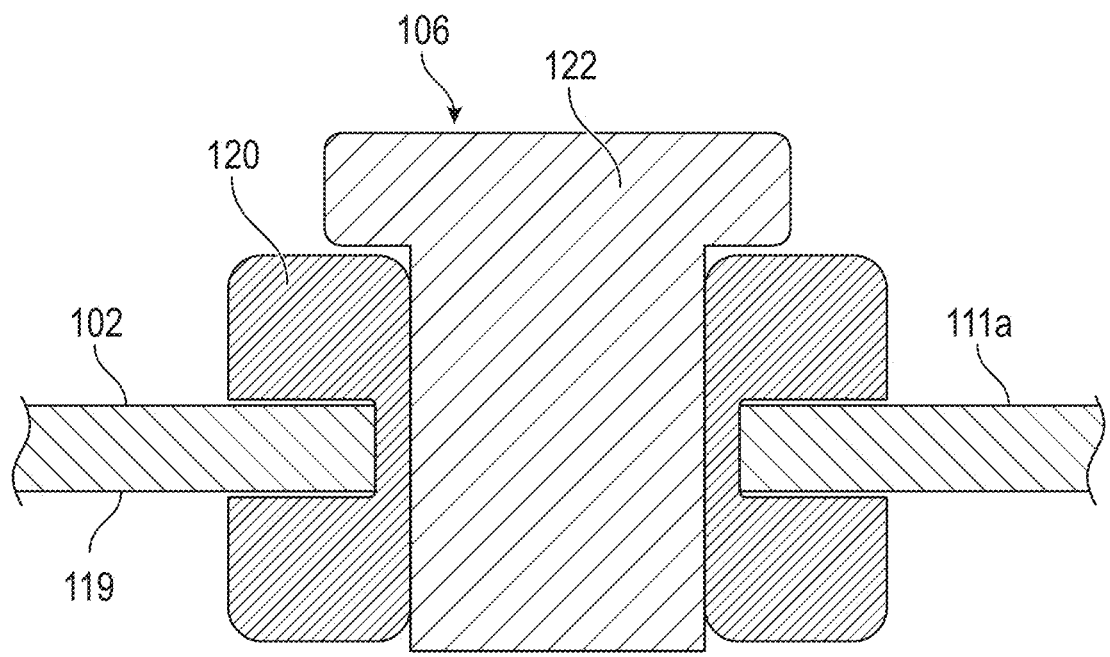
FIGS. 12 and 13 are cross-sectional views of an exemplary portal including a grommet for the thermal retention covering of FIGS. 8-10.
Figure 13:
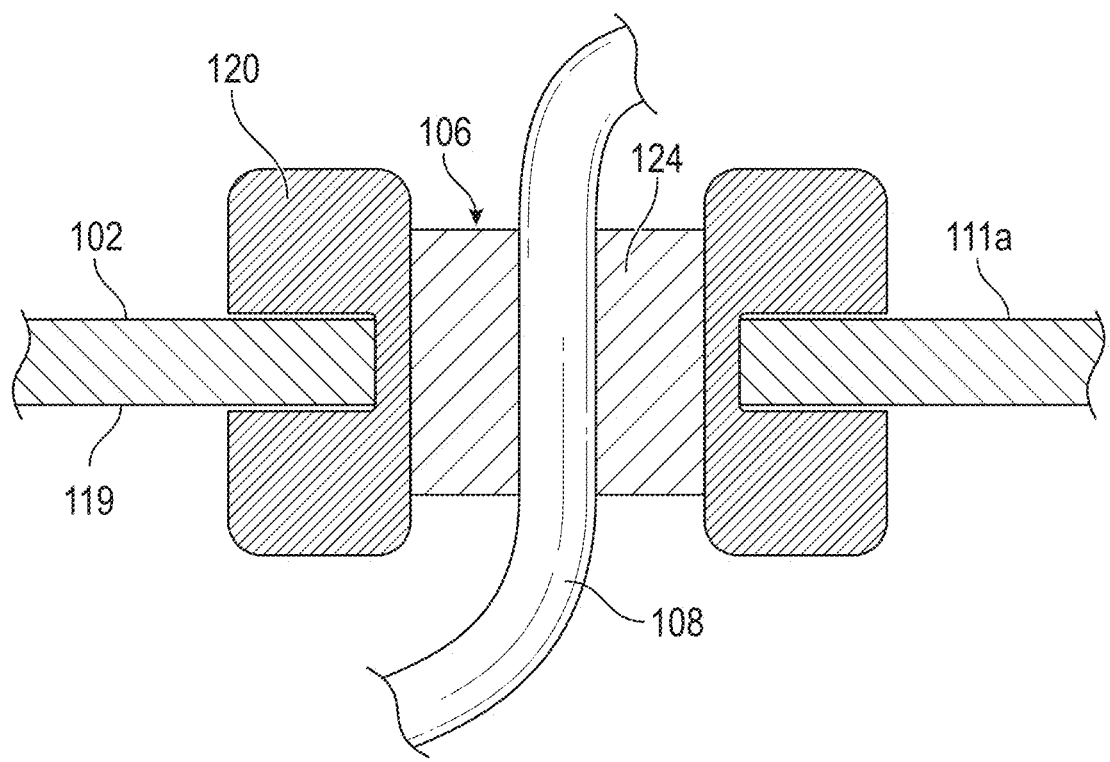

In some examples, the thermal retention covering 100 can include a plug 122 that can be inserted into the interior space of the grommet to seal the portal when the temperature probe is not inserted through the portal, such as when the thermal retention covering is stored and/or utilized without a temperature probe (FIG. 12). In some examples, the grommet 120 can include a resiliently deformable sealing member 124 disposed within the central space of the grommet, such as a rubber or silicone plug having one or more slits through which the temperature probe 108 can be inserted (FIG. 13). The sealing member can form seal around the inserted temperature probe and/or can seal the patient side surface when the thermal retention covering is stored and/or utilized without a temperature probe. In some examples, the plug 122 and/or the sealing member 124 can prevent inflow of fluid into the interior space 110, such as, for example, preventing inflow of a cleaning fluid during cleaning of the covering 100, preventing inflow of patient fluids (e.g., sweat, urine, blood, etc.) during use of the covering 100 with a patient, and/or other scenarios where the covering 100 is exposed to a fluid. In other examples, the plug and/or the seal can be excluded.

In some examples, the temperature probe 108 can be permanently attached to the thermal retention covering 100. For example, the distal end portion of the probe can be adhered or welded to the material of the outer shell layer 111a surrounding the portal 106 or the grommet 120. In another example, the temperature probe can be inserted between the two outer fluid impermeable layers or outer shell layers 111 (i.e., layers 111a, 111b) and can be attached to the weld between the outer shell layers at the perimeter of the covering. The temperature probe can be secured or attached to the covering such that the probe tip is at a desired location within the interior space (for example, at a center of the covering). For example, the probe can be adhered or welded to the interior surface 119 of the outer shell layer 111a or otherwise attached to the interior surface 119.

In some examples, in a general use version of the thermal retention covering (including a heat reflective layer), the covering can be used in, for example, anesthetic induction, preoperative prep, surgery, postoperative recovery, X-ray and CT scanning. In each of clinical situations the measurement of the patient surface or skin can be hampered or affected by:
  ambient cool air temperature in the operating or radiology room
  ambient cool air flow in the operating or radiology room
  ambient humidity of the operating or radiology room
  patient movement
  movement or dislodgement of the temperature probe
  patient perspiration
  patient body fluids In each of these clinical situations the thermal retention covering can be either draped over or circumferentially wrapped around the entire or a portion of the patient. Prior to draping or circumferentially wrapping, the tip of a temperature probe, for example, a thermocouple probe approximately 36 inches long, is passed into the temperature probe access portal approximately 1 to 2 inches. The diameter of the portal can be about the same diameter as the temperature probe. Accordingly, the temperature probe can be kept in place by friction between the probe and the portal. The thermal retention covering is then be draped over the patient or circumferentially wrapped in a manner that provides for the most intimate contact of the portion of the thermal retention covering having the temperature probe access portal with the patient skin surface. The remaining portion of the temperature probe can be passed under the thermal retention covering to a temperature monitor which is placed in a manner where temperature readings are easily visualized. Examples of temperature monitors with lengthy thermocouple probes that could be used are the VetLife® PT and the Data Therm II. With the tip of the temperature probe between the patient side external material and the immediately adjacent heat reflective layer, it is disposed in a protected microenvironment. At steady state this environment will now be the same temperature as the patient surface and will not be subject to the temperature measurement challenges brought about by the ambient environment, patient movement and patient factors as described above.

In some examples, in an MRI-compatible or safe version of the thermal retention covering 100, the thermal retention covering can be utilized in the MRI scanning environment. The magnetic field strength of an MRI scanner precludes the use of conventional patient vital sign monitors because of their ferromagnetic components. The electromagnetic interference provided by the MRI magnet creates measurement errors in conventional patient monitors. Additionally, the monitor itself can become a projectile if placed too close to the MRI magnet because of the ferromagnetic attraction of its components. The magnetic field strength of an MRI scanner is measured in Tesla units. One Tesla (T) is equal to 10,000 Gauss (G) units. MRI scanners in clinical use today are 1.5 T, 2 T and 3 T in strength. The quality of the image is directly related to the strength of the magnetic field.

The 5 Gauss line in an MRI scanner room is the safety line drawn around the perimeter of the main magnet of the MRI scanner specifying the distance at which the magnetic field is equivalent to 5 Gauss (0.0005T). This line in a 1.5 T MRI scanner would be 12 meters (39 feet) in a non-shielded MRI scanner from the center of the magnet. A 3 T MRI scanner would have a 5 Gauss line even further from the magnet. At 5 Gauss and above or closer to the MRI scanner, cardiac pacemakers, other implanted electronic devices and electronic patient monitors are subject to interference by the magnetic field of the MRI scanner. At the 5 Gauss line ferromagnetic materials may become projectiles risking injury to the patient in the scanner and medical personnel close to the scanner.

Any hardware thermistors and thermocouples are prone to measurement errors due to MRI electromagnetic interference and usually cannot be used in the MRI environment. Fiberoptic temperature sensors can be used in the MRI environment because they are not made of ferromagnetic materials and are not affected by electromagnetic interference. Since conventional patient vital sign monitors cannot be used in the MRI environment, a fiberoptic temperature probe must provide its temperature measurement by one of the three current methods below.
  1. The fiberoptic temperature probe can run from the patient across the MRI scanner room through a magnetically shielded port in the MRI control room wall to a patient temperature monitor in the MRI control room. Fiberoptic probes of this type can be up to 50 meters (164 feet) long.
  2. The fiberoptic temperature probe can be connected to an MRI compatible transmitter which is close to the patient. The transmitter sends a radio signal to a patient monitor in the MRI control room which displays the patient temperature.
  3. The fiberoptic temperature probe can be connected directly to an MRI compatible patient monitor which can be close to the MRI scanner and not affected by the electromagnetic field.

The fiberoptic probe, connected to the patient monitor by any of the above three methods, can be used to measure skin or surface and core patient body temperature. The skin temperature measurement sites can be the axilla, groin and nares whereas the core temperature can be measured utilizing the esophagus and rectum.

Normally, pediatric and veterinary patients are given general anesthesia for MRI procedures. MRI scans can last from 1½ to 2 hours and general anesthesia is necessary to prevent patient movement, patient anxiety, claustrophobia and above all, airway protection in an environment where patient access is difficult. General anesthesia predisposes the patient to hypothermia because of the loss of neurogenic body temperature control. The ambient MRI room temperature for optimal magnet operation is usually 18 degrees C. and very low humidity of 45 percent which hastens body heat loss. Additionally, to keep the magnet cool for optimal operation, a cooling fan is continually blowing cool air through the center of the magnet further contributing to patient body heat loss. One study showed that 63 percent of pediatric patients became hypothermic (less than 36 degrees C.) during MRI scanning.

The MRI environment makes it difficult to monitor the temperature of the patient even with a fiberoptic temperature probe. Patient access is difficult since the patient is in the MRI scanner with no one else in the room, enveloped in the center of the magnet and moving through the scanner. Measurement of the skin by the fiberoptic probe can be in sites like the axilla, groin and nares. Temperature measurement of the skin can be affected by:
  Patient movement as the patient moves through the MRI scanner
  Ambient room temperature of 18 degrees C.
  Ambient humidity of 45 percent
  MRI cooling fan
  Patient perspiration
  Patient body fluids
  Peripheral vasoconstriction Without a fiberoptic temperature probe, a non-magnetic liquid crystal display can be utilized which is a small sticker which is placed on the forehead. Since there is limited or no patient access, however, this method has no practical utility during MRI scanning.

It has been shown above that the patient being in the MRI scanner and the MRI environment itself creates difficulties with patient access, predisposes the patient to hypothermia and the use of temperature measurement sites on the skin are fraught with temperature measurement errors. As discussed above, an MRI-compatible version of the thermal retention covering, having internal patient side open cell foam or heat trapping layer and its adjacent fibrous or heat insulative layer, can provide and/or maintain normothermia in the MRI environment.

The MRI-compatible version of the thermal retention covering 100 including the portal 106 provides for a microenvironment in which accurate patient surface or skin temperature measurement can occur. When the tip or temperature sensor of the fiberoptic temperature probe is passed into the portal and advanced several inches it is held securely in place by the friction between the internal diameter of the portal or portal grommet and the fiberoptic temperature probe to prevent probe movement as the patient moves through the MRI scanner. The length of the fiberoptic probe then runs along the patient side of the thermal retention covering and to a patient monitor in one of the three methods previously described. With the fiberoptic temperature probe securely in place through the portal and in between the external patient side external material and the adjacent heat trapping or open cell layer, patient access for temperature measurement is no longer a challenge as the temperature values can be clearly seen by practitioners on the patient monitor. The microenvironment created by the space between the patient side external material and the adjacent heat trapping layer can limit or prevent effect of the 18 degree C. ambient temperature, 45 percent humidity, and/or the MRI cooling fan on monitoring of the patient temperature. This microenvironment can also limit or prevent temperature measurement errors caused by patient perspiration, patient body fluids, and/or peripheral vasoconstriction.

The portal can be in one location on the patient side of the MRI-compatible thermal retention covering or portals can be made at multiple sites on the patient side to provide temperature site options dependent on the clinical situation and/or the patient anatomy. The patient is typically given the anesthetic induction outside the MRI scanner room. The fiberoptic temperature probe is passed into the appropriate patient side portal and advanced as described above. The patient is then circumferentially wrapped with the MRI-compatible thermal retention covering in a manner which provides the most intimate contact with portal and the temperature probe. The patient is then placed in the scanner along with all the MRI compatible anesthesia and the fiberoptic temperature probe is connected to the patient monitor in one of the three methods described above.

In some examples, the thermal retention covering 100 can be designed for use in survival and/or search and rescue settings. In such examples, the thermal retention covering can include the two outer fluid impermeable layers or shells 111. Internal of the shell layers, immediately adjacent to the patient side surface 102 can be a heat reflective or heat radiant layer next to which is a heat trapping or open cell foam layer, and adjacent to the heat trapping or open cell foam layer can be a heat insulative or fibrous insulating layer.

The extreme environmental and patient management challenges in survival and search and rescue situations make temperature measurement of the patient's core and peripheral or skin temperature very difficult. The patient's core temperature by the esophageal or rectal route is very difficult because of relative inaccessibility to these sites as well as the patient usually being awake and intolerant of an invasive temperature measurement. The measurement of the skin or peripheral patient temperature is also difficult and can produce erroneous measurements because of, but not limited to:
  Environmental issues, such as
    wind
    rain
    snow
    humidity
  Patient issues, such as
    body fluids
    vasoconstriction of the skin in hypothermia
    wet clothing
    access to appropriate skin temperature monitoring sites The portal 106 can be disposed the patient side surface 102 of the covering 100. It can be placed in a single location where it is most likely to be the most clinically useful or can include portals at multiple locations on the patient side of the covering to provide multiple measuring site options. A flexible temperature probe 108 can be passed through the portal 106 and advanced several inches with the length of the flexible probe extending along the width or length of the patient side of the covering to a portable temperature monitor. The thermal retention covering 100 is then draped over, circumferentially wrapped or placed under the patient in a manner in which the covering provides the greatest warming benefit for the patient and the greatest intimate contact of the portal, now containing the temperature probe, with the patient surface.

The portal 106 and the interior space 110 provides for a microenvironment between the patient side external material and the immediately adjacent heat reflective layer. With the probe temperature sensor in this protected microenvironment, it is protected from and/or no longer subject to the environmental and patient issues and erroneous temperature measurements as described above. In these search and rescue situations, medical personnel may attempt to normalize the patient's body temperature using multiple techniques. Therefore, in addition to monitoring the patient's peripheral or skin temperature, the temperature probe in the microenvironment created by the portal, also gives medical personnel an indication as to the effectiveness of their patient warming efforts. With the length of the temperature probe running on the patient side of the Covering to a portable temperature monitor such as the Data Therm II, the reading of the patient's peripheral temperature is readily accessible.

During the course of patient care, active warming may need to be utilized to maintain or elevate a patient's body temperature. Active warming devices may include but not limited to chemical warming packs, electrical warming pads and forced warm air pads and blankets which may be utilized under, over and around the patient. These active warming devices may be used in combination with the thermal retention covering 100 to maintain and elevate the patient's surface temperature. The effectiveness of these patient warming efforts can be monitored and/or evaluated based on the temperature measurements.

For purposes of this description, certain aspects, advantages, and novel features of the embodiments of this disclosure are described herein. The disclosed apparatuses, systems, and methods should not be construed as limiting in any way. Instead, the present disclosure is directed toward all novel and nonobvious features and aspects of the various disclosed embodiments, alone and in various combinations and sub-combinations with one another. The disclosed embodiments are not limited to any specific aspect or feature or combination thereof, nor do the disclosed embodiments require that any one or more specific advantages be present or problems be solved.

As used herein, the term "and/or" used between the last two of a list of elements means any one or more of the listed elements. For example, the phrase "A, B, and/or C" means "A," "B," "C," "A and B," "A and C," "B and C" or "A, B and C." As used herein, the term "coupled" generally means mechanically, chemically, electrically, magnetically or otherwise coupled or linked and does not exclude the presence of intermediate elements between the coupled items, unless otherwise described herein.

In view of the many possible embodiments to which the principles disclosed herein may be applied, it should be recognized that the illustrated embodiments are only examples and should not be taken as limiting the scope of the disclosure. Rather, the scope of the disclosure is at least as broad as the following claims. I therefore claim all that comes within the scope and spirit of these claims.

The invention claimed is:

1. A thermal retention covering, comprising:
a flexible fluid-impermeable outer shell having two outer layers sealed at a perimeter of the flexible fluid-impermeable outer shell, a first one of the outer layers forming a patient side surface configured to be oriented toward a patient;
two or more inner layers disposed between the two outer layers, the two or more inner layers comprising two or more of:
a flexible radiant barrier layer positioned inside the outer shell, the radiant barrier layer being reflective of radiant energy;
a flexible thermal insulation layer positioned inside the outer shell adjacent the radiant barrier layer, the thermal insulation layer comprising a material having low thermal conductivity and providing insulation against conduction of heat through the thermal retention covering; or
a flexible air cell layer positioned inside the outer shell, the air cell layer comprising a plurality of cells containing air and configured to create a heat insulating layer of air within the outer shell to prevent heat loss through the thermal retention covering; and
a portal formed in the patient side surface and in communication with an interior space between the first outer layer and the two or more inner layers, wherein the portal is a first one of a plurality of portals in the patient side surface and in communication with the interior space between the first outer layer and the two or more inner layers, wherein the plurality of portals enables use of a selected area of the thermal retention covering for taking a temperature reading;
wherein the thermal retention covering is configured to retain patient body heat; and
wherein the portal is sized and shaped to receive a temperature probe therethrough for insertion of the temperature probe into the interior space between the first outer layer and the two or more inner layers.

2. The thermal retention covering of claim 1, further comprising a temperature probe, wherein a distal end portion of the temperature probe is configured to be inserted through the portal into the interior space between the first outer layer and the two or more inner layers.

3. The thermal retention covering of claim 1, wherein the portal comprises a grommet.

4. The thermal retention covering of claim 3, wherein the grommet is heat welded to the first outer layer at a perimeter region of the portal.

5. The thermal retention covering of claim 3, wherein the grommet comprises a seal disposed within an opening of the grommet for sealing the interior space, wherein the seal includes a slit for insertion of the temperature probe therethrough.

6. The thermal retention covering of claim 3, further comprising a plug for insertion into the grommet to seal the interior space when the temperature probe is not inserted through the portal.

7. The thermal retention covering of claim 3, wherein the grommet forms a first raised annular structure that extends outwards from the patient side surface, and a second raised annular structure that extends inwards from the interior surface of the first outer layer.

8. The thermal retention covering of claim 3, wherein the grommet is configured to retain a position of the temperature probe relative to the grommet via frictional forces between the grommet and an exterior surface of the temperature probe.

9. The thermal retention covering of claim 1, wherein portal enables temperature monitoring of the patient in a protected microenvironment formed by the interior space between the first outer layer and the two or more inner layers.

10. A method of utilizing the thermal retention covering of claim 1, the method comprising:
    anesthetizing the patient;
    inserting a distal end portion of the temperature probe through the portal and into the interior space between the first outer layer and the two or more inner layers;
    orienting the patient side surface toward the patient;
    wrapping the thermal retention covering around the anesthetized patient; and
    monitoring a patient temperature during a medical procedure.

11. A method of utilizing the thermal retention covering of claim 1, the method comprising:
    applying one or more heating techniques to the patient;
    inserting a distal end portion of the temperature probe through the portal and into the interior space between the first outer layer and the two or more inner layers;
    orienting the patient side surface toward the patient;
    wrapping the thermal retention covering around the patient;
    monitoring a patient temperature over time; and
    evaluating effectiveness of the one or more heating techniques based on the monitoring of the temperature.

12. An MRI-compatible thermal retention covering assembly, comprising:
    an MRI-compatible temperature probe; and
    a thermal retention covering comprising:
        a flexible fluid-impermeable outer shell having two outer layers sealed at a perimeter of the flexible fluid-impermeable outer shell, a first one of the outer layers defining a patient side surface configured to be oriented toward a patient;
        an insulation layer disposed within the outer shell, the insulation layer comprising:
            a flexible air cell layer positioned inside the outer shell, the air cell layer comprising a plurality of cells containing air and configured to create a heat insulating layer of air within the outer shell to prevent heat loss; and
            a flexible thermal insulation layer positioned inside the outer shell adjacent the flexible air cell layer, the thermal insulation layer comprising a fibrous material having low thermal conductivity and providing insulation against conduction of heat through the thermal retention covering; and
        a portal formed in the patient side surface and in communication with an interior space between the first outer layer and the insulation layer;
        wherein the portal is sized and shaped to receive a distal portion of the MRI-compatible temperature probe therethrough for insertion of the temperature probe into the interior space between the first outer layer and the insulation layer.

13. The assembly of claim 12, wherein the portal comprises a grommet.

14. The assembly of claim 13, wherein the grommet is configured to retain a position of the temperature probe relative to the grommet via frictional forces between the grommet and an exterior surface of the temperature probe.

15. The assembly of claim 12, wherein portal enables temperature monitoring of the patient in a protected microenvironment formed by the interior space between the first outer layer and the insulation layer.

16. The assembly of claim 12, wherein the MRI-compatible temperature probe comprises a fiberoptic temperature probe.

17. The assembly of claim 16, wherein the fiberoptic temperature probe is configured for communication with one or more of an MRI-compatible transmitter or an MRI-compatible monitor.

18. The assembly of claim 12, wherein a diameter of the portal is equal to a diameter of the temperature probe.

19. The assembly of claim 12, wherein a diameter of the portal is in a range of 1 mm to 10 mm greater than a diameter of the temperature probe.

* * * * *